United States Patent [19]

Tolliver et al.

[11] 3,997,327

[45] Dec. 14, 1976

[54] DENTAL COMPOSITION

[75] Inventors: Albert Tolliver, Summit, N.J.; Joseph Aliotta, Staten Island; Louis F. Alcuri, Brooklyn, both of N.Y.

[73] Assignee: Engelhard Minerals & Chemicals Corporation, Murray Hill, N.J.

[22] Filed: Dec. 29, 1975

[21] Appl. No.: 644,872

[52] U.S. Cl. .................................. .5 R; 75/169; 75/173 R; 75/173 C
[51] Int. Cl.$^2$ .................................... C22C 5/06
[58] Field of Search ............ 75/.5 R, 173 C, 173 R, 75/134 N, 134 C, 169

[56] References Cited

UNITED STATES PATENTS

| 1,963,085 | 6/1934 | Gray | 75/173 C |
|---|---|---|---|
| 2,281,991 | 5/1942 | Poetschke | 75/173 C |
| 3,305,356 | 2/1967 | Youdelis | 75/173 C X |
| 3,841,860 | 10/1974 | Wolf | 75/.5 R |
| 3,871,876 | 3/1975 | Asgar et al. | 75/169 |
| 3,933,961 | 1/1976 | Burns | 75/169 X |
| 3,954,457 | 5/1976 | Weikel | 75/169 |

*Primary Examiner*—L. Dewayne Rutledge
*Assistant Examiner*—E. L. Weise

[57] ABSTRACT

A novel dental composition comprises an admixture of two forms of a powdered alloy in specified proportions, i.e., a major proportion in the form of relatively smooth spheroidal particles, e.g., spheres, and a minor proportion in the form of relatively rough, irregularly shaped particles, e.g., flakes. The resulting dental composition requires less mercury for amalgamation and exhibits enhanced physical properties and handling characteristics.

7 Claims, 3 Drawing Figures

DENTAL COMPOSITION

This invention relates to new dental amalgam compositions and to the preparation thereof. More specifically, it relates to a uniform admixture of specified proportions of two forms of a powdered alloy, e.g., spheres and flakes, which requires less mercury for amalgamation and which exhibits enhanced physical properties and handling characteristics.

BACKGROUND

Dental amalgams are produced by intimately combining mercury with dental amalgam alloys, such as an alloy containing about 55–75% by weight silver, 20–40% tin, 0–10% copper and 0–2% zinc. Upon reaction with mercury using known dental clinical techniques, a plastic mass is produced which quickly sets into a hard rigid body. While the mass is plastic, it may be packed into a surgically prepared tooth and carved or otherwise worked into a desired conformation, thereby restoring the anatomy and function of the tooth.

Heretofore such alloys consisted of powder in the form of irregularly shaped microgranules, flakes or filings or powder in the form of spheroidal particles. The trend toward use of spheroidal powder was generated by the dentists' desire to reduce packing pressure or condensation and to minimize the amount of mercury required in the amalgamation of the powder. Amalgams made from spheroidal particles also have the desirable attribute of a higher diametral tensile strength than amalgams made from microgranules, flakes or filings and also generate less expressed mercury prior to placement in tooth cavities.

Amalgams made from spheroidal powder, however, exhibit an undesirable feature. When the dentist attempts to pack them within a cavity there is a tendency for the amalgam to ride up along walls of cavity and not pack as firmly as amalgams made from filings for microgranules.

OBJECTS OF THE INVENTION

It is therefore a general object of this invention to provide an improved dental amalgam composition which copes with the aforementioned problems of both spheroidal amalgams and amalgams made from microgranules, flakes or filings.

It is another general object to provide an amalgam having the desirable features of both spheroidal amalgams and amalgams made from microgranules, flakes or filing.

It is another general object to provide an amalgamable dental composition which can be prepared or manufactured employing conventional techniques.

It is a specific object to provide a dental composition which requires less mercury for amalgamation, generates less expressed mercury prior to placement in a tooth cavity and permits reduced packing pressures.

It is another specific object to provide a dental amalgam of enhanced physical properties which is substantially free of any tendency to ride up along walls of a cavity and not pack as firmly as desired.

These and other objects will become apparent as the detailed description proceeds.

DESCRIPTION OF THE INVENTION

The new and improved dental amalgam compositions of this invention comprise a substantially uniform, comminuted admixture of a major proportion of the desired alloy in spheroidal form and a minor proportion thereof in the form of irregularly shaped particles such as microgranules, flakes or filings. The alloy employed in this invention is any certified or hereafter certified by the American Dental Association for dental amalgams. It may comprise, for example, the aforementioned silver, tin, copper and zinc alloy with silver present in the range of about 55 to 75% by weight, tin in the range of about 20 to 40% by weight, copper in the range of about 0 to 10% by weight, and zinc in the range of about 0 to 2% by weight. Other alloying ingredients may also be present to achieve particular characteristics.

As above indicated, the alloy is present in spheroidal form as a major proportion of the composition, i.e., more than about 50% by weight, e.g., about 55 to about 90% of the composition by weight, optimally about 60%. The alloy is also present in the form of irregularly shaped particles as a minor proportion, i.e., less than about 50% by weight, e.g., about 10 to about 45% by weight, optimally about 40%. In an optimal case, 60 parts spheroids are substantially uniformly admixed with 40 parts irregularly shaped particles to produce 100 parts of the composition suitable for subsequent amalgamation with mercury.

The term "spheroidal" as used herein means that the individual particles are spheres or shaped like a spheroid, that is, are approximately spherical, and usually with a relatively smooth surface. A particle is approximately spherical if the largest dimension is no greater than about 130% of the smallest dimension. Processes for producing alloys in spheroidal form are known to those skilled in the art. The term spheroidal will be more clearly understood from a consideration of the photomicrographs hereinafter referenced.

The term "irregularly shaped" as used herein means that the individual particles are substantially multi-sided and generally angularly shaped or rectilinear, albeit irregular, and usually with rough or otherwise relatively non-smooth surfaces. Typically, they are in the form of what is variously referred to in the art as microcut material, lathe-cut material, platelets or filings. Conventional microcutting, lathe cutting or filing techniques can be employed satisfactorily to obtain the irregularly shaped particles and are well known to those skilled in the art. The term irregularly shaped will be more clearly understood from a consideration of said photomicrographs hereinafter referenced.

The particle size distribution of both forms of the alloy is normally within the range of about 1 to about 100 microns, e.g., about 2 to about 80 microns, preferably about 5 to about 40 mircrons. The particle size range designation means that substantially all of the particles will pass a sieve or screen having openings corresponding to the larger size and substantially all of the particles will be retained on a sieve or screen having openings corresponding to the smaller size. The average particle size is typically in the range of about 20 to 30 microns, although the invention is not necessarily limited thereto.

To form a dental amalgam composition in accordance with this invention a major proportion of the spheroids and a minor proportion of the irregularly-shaped particulates are mechanically or manually mixed to produce a substantially uniform blend. In the preferred mechanical embodiment, the two alloys are mechanically mixed in a conventional blender for at least about 15 minutes, e.g., about ½ hour to about 1 ½ hours, typically about 1 hour. For dental use, the complete amalgam admixture is triturated with mercury in amounts of from about 0.8:1 up to about 1.5:1 parts of mercury by weight per part of the alloy powder. Preferably mercury is employed in a ration of from about 0.9:1 to about 1.4:1 parts of mercury by weight per part of alloy powder, optimally a ratio of about 1:1. A feature of the present invention is that the blended composition requires less mercury for amalgamation than an equivalent weight of either of the two powdered ingredients forming the blend.

Conventional trituration equipment and techniques may be employed, such as the condensation technique of the American Dental Association Specification No. 1 for dental amalgams. Typically, a mixing or trituration time of about 3-12 seconds at an amalgamator speed of about 3,000 to 5,000 revolutions per minute may be employed, e.g., a one-spill mixing time of about 5 seconds at about 3,500 revolutions per minute

DESCRIPTION OF THE DRAWING

The present invention will be more clearly understood from the accompanying drawing, wherein:

Referring to FIG. 1, it is apparent that the spheroidal particles are approximately spherical and often exhibit a relatively smooth surface structure. The particles vary considerably in size, substantially all, however, falling within the range of about 1 to about 100 microns.

Figure 1:
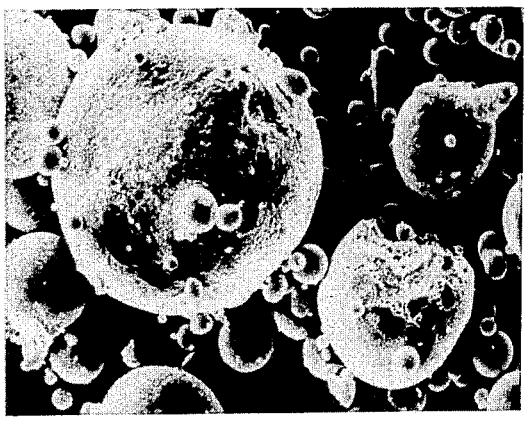
FIG. 1 is a scanning electron microscope photomicrograph of the spheroidal alloy particles which make up a major proportion of the blended dental composition of the present invention.
Figure 2:
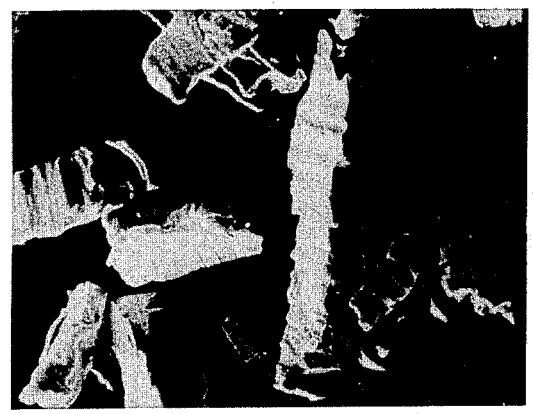
FIG. 2 is a similar photomicrograph of the irregularly shaped alloy microgranules which make up a minor proportion of the blended dental composition of the present invention.

In contrast, the microgranules of FIG. 2 are irregularly shaped and angular and exhibit a relatively rough surface structure. The individual particles vary connsiderably in size, although the variation is not as pronounced as in the case of the spheroidal particles of FIG. 1. All fall within the range of about 1 to 100 microns and substantially all fall within the range of about 2 to 60 microns.

Figure 3:
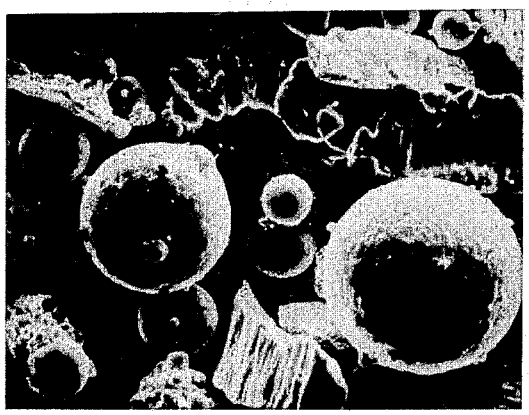
FIG. 3 is a similar photomicrograph of the blended dental composition of the present invention prepared by blending particles having the forms illustrated in FIGS. 1 and 2.

When the particles having the form illustrated in FIGS. 1 and 2 are uniformly blended in the major and minor proportions contemplated by the present invention, the result is as depicted in FIG. 3. The blend is optimal, that is, approximatley 60% spheroidal and 40% microgranular. Because of the extreme magnification, e.g., about 300–500 times, and small field of view, the substantial homogeneity of the blend is not readily apparent in FIG. 3.

The following examples further illustrate the present invention or provide comparative information and data which point up the advantages of the present invention.

EXAMPLE 1

A particularly preferred embodiment of the present invention was prepared by mechanically admixing 60% by weight of spheroidal particles, substantially as depicted in FIG. 1, with 40% by weight of microgranules, substantially as depicted in FIG. 2, the resulting uniform blend, substantially as depicted in FIG. 3, having an average particle size of about 24 to 28 microns and a particle size distribution predominantly in the range of about 2 to 60 microns. The composition of the alloy in each case was approximately as follows:

| Silver | 68 | Wt.% |
|---|---|---|
| Tin | 27 | Wt.% |
| Copper | 4.4 | Wt.% |
| Zinc | 0.6 | Wt.% |

The resulting powdered dental composition was triturated in conventional manner with about 1 part by weight of mercury per part of the blend utilizing mechanical trituration for about 5 to 10 seconds. The resulting amalgam exhibited the following characteristics:

| | |
|---|---|
| Average Diametral Tensile Strength at 15 Minutes | 920 psi |
| Average 1-Hour Compression Strength | 20,000 psi |
| Flow (24 Hours) | 1.05% |
| Dimensional Change at 24 Hours | +3.8 Microns/cm |
| Working Time | 3 to 5 minutes |
| Carving Time | Up to 5 minutes |

The diametral tensile strength of the composition at 15 minutes was at least 20% greater than the strength of an amalgam prepared using only microgranules. The amalgam packs solidly for excellent marginal integrity and easy carving. The combination of spheroids and microgranules locks the amalgam more firmly in place, thereby preventing cluster roll-off.

Further illustrative examples are as follows:

EXAMPLE 2

An amalgamable dental composition in accordance with the invention is prepared by mechanically admixing particulates of an alloy in the proportion of 55% by weight spheroidal form having a particle size distribution in the range of about 2 to 90 microns and 45% by weight of irregularly shaped microgranules having a particle size distribution of about 5 to 40 microns. The alloy has the following composition:

| Silver | 60 | Wt.% |
|---|---|---|
| Tin | 34 | Wt.% |
| Copper | 5.2 | Wt.% |
| Zinc | 0.8 | Wt.% |

The resulting powdered dental composition is triturated in conventional manner with about 1 part by weight of mercury per part of composition, using the condensation technique of the American Dental Association Specification No. 1 for dental amalgams.

EXAMPLE 3

An amalgamable dental composition in accordance with the invention is prepared by mechanically admixing particulates of an alloy in the proportion of 70% by weight spheroidal form having a particle size distribution in the range of about 1 to 100 microns and 30% by weight of irregularly shaped microgranules having a particle size distribution of about 4 to 35 microns. The alloy has the following composition:

| Silver | 70 | Wt.% |
|---|---|---|
| Tin | 24 | Wt.% |
| Copper | 5.4 | Wt.% |
| Zinc | .6 | Wt.% |

The resulting powdered dental composition is triturated in conventional manner with about 1.1. part by weight of mercury per part of composition, using the condensation technique of the American Dental Association Specification No. 1 for dental amalgams.

EXAMPLE 4

An amalgamable dental composition in accordance with the invention is prepared by mechanically admixing particulates of an alloy in the proportion of 65% by weight spheroidal form having a particle size distribution in the range of about 2 to 90 microns and 35% by weight of irregularly shaped microgranules having a particle size distribution of about 2 to 60 microns. The alloy has the following composition:

| Silver | 65 | Wt.% |
|---|---|---|
| Tin | 28 | Wt.% |
| Copper | 6.4 | Wt.% |
| Zinc | .6 | Wt.% |

The resulting powdered dental compositon is triturated in conventional manner with about 1.05 parts by weight of mercury per part of composition, using the condensation technique of the American Dental Association Specification No. 1 for dental amalgams.

While it is essential that the dental composition of this invention be in the form of a mixture of spheroidal and irregularly shaped particulates when used, and may be supplied in such form when supplied, it should be understood that for distribution purposes the two forms of the alloy can be supplied separately and admixed by the ultimate user in the required proportions. Alternatively, the two admixed forms in the required proportions can be pressed into tablet or capsule form for convenience.

While only certain embodiments have been set forth, alternative embodiments and various modifications of the embodiments depicted will be apparent from the above description to those skilled in the art. These and other alternatives are considered equivalents and within the spirit and scope of the present invention.

Having described the invention, what is claimed is:

1. A composition adapted for amalgamation with mercury to form a dental amalgam comprising an alloy consisting essentailly of about 55 to 75% by weight silver, about 20 to 40% by weight tin, about 0 to 10% by weight copper, and about 0 to 2% by weight zinc, said alloy being in particulate form having a particle size distribution in the range of about 1 to 100 microns, a major proportion of the particulates being spheroidal in shaped and a minor proportion thereof being substantiallty irregularly shaped.

2. The composition of claim 1 wherein about 55 to 90% by weight of the composition is in the form of spheroidal particles and about 10 to 45% by weight is in the form of irregularly shaped particles.

3. The composition of claim 1 wherein about 60% by weight of the composition is in the form of spheroidal particles and about 40% by weight is in the form of irregularly-shaped particles.

4. The composition of claim 1 amalgamated with about 0.8:1 to 1.5:1 parts of mercury by weight per part of composition.

5. A process for preparing a dental amalgam which comprises triturating the composition of claim 1 with sufficient mercury to form a workable plastic amalgam.

6. A dental composition comprising an alloy consisting essentially of about 55 to 75% by weight silver, about 20 to 40% by weight tin, about 0 to 10% by weight copper and about 0 to 2% by weight zinc, said alloy being in particulate form having a particle size distribution substantially in the range of about 2 to 80 microns, about 55 to 90% by weight of the particles being spheroidal and about 10 to 45% by weight of the particles being irregularly shaped, both forms being substantially uniformly blended throughout the composition.

7. A process for preparing a dental amalgam which comprises triturating the composition of claim 6 with about 1 part of mercury by weight per part of composition to form a dental amalgam.

* * * * *